(12) United States Patent
Ledeboer

(10) Patent No.: US 7,696,418 B2
(45) Date of Patent: Apr. 13, 2010

(54) SPREADING RYEGRASS

(75) Inventor: Fred Ledeboer, Aurora, OR (US)

(73) Assignee: Ledeboer Seed, LLC, Aurora, OR (US)

( * ) Notice: Subject to any disclaimer, the term of this patent is extended or adjusted under 35 U.S.C. 154(b) by 0 days.

(21) Appl. No.: 12/168,239

(22) Filed: Jul. 7, 2008

(65) Prior Publication Data

US 2009/0178164 A1  Jul. 9, 2009

Related U.S. Application Data

(60) Provisional application No. 61/019,655, filed on Jan. 8, 2008.

(51) Int. Cl.
*A01H 5/00* (2006.01)
(52) U.S. Cl. .................................... 800/323
(58) Field of Classification Search .............. 800/295, 800/323
See application file for complete search history.

(56) References Cited

OTHER PUBLICATIONS

Holland. United States Plant Variety Protection Certificate No. 8300016, Jul. 25, 1984.*
A redacted the agreement titled "Exclusive License Agreement", 4 pages, Mar. 2006.
United States Plant Variety Protection No. 8300016, Titled Perennial Ryegrass 'Barclay', Jul. 25, 1984.

* cited by examiner

*Primary Examiner*—Anne Marie Grunberg
*Assistant Examiner*—Keith O. Robinson
(74) *Attorney, Agent, or Firm*—Jondle & Associates, P.C.

(57) ABSTRACT

Perennial ryegrass plants with a spreading habit are provided. The perennial ryegrass plants of the present invention display a growth habit with intertwining tillers that form a very dense sward of 10,000 tillers or more per square foot within one growing season. The ryegrass plants of the present invention also display secondary tillers, something not seen in currently available commercial perennial ryegrass varieties. The spreading growth habit of the plants of the present invention makes a very attractive turfgrass when grown for turf and also provides high seed production.

24 Claims, No Drawings

SPREADING RYEGRASS

CROSS-REFERENCE

This application claims the benefit of priority to U.S. Provisional Application No. 61/019,655 filed on Jan. 8, 2008 which is herein incorporated by reference.

BACKGROUND

The present invention relates to perennial ryegrass with a spreading growth habit. All publications cited in this application are herein incorporated by reference.

Turfgrass plays a major role in our daily life. Turfgrass, from a beautification standpoint, provides a canvas for landscaped areas contributing to aesthetic appeal and adding to economic value. Recreational facilities include an array of sports fields, golf courses, parks and lawns. Turfgrass also provides functional value including dust control, erosion control, and glare reduction.

Use and appearance are prime considerations for turfgrass. To best serve a particular function, the turf should be suitable for the use for which it is intended and aesthetically appealing. It should also be well-adapted to the environment where it will be planted. Based on climatic adaptation, turfgrass species have been placed into four categories: adapted for cool humid regions, warm humid regions, cool arid regions, and warm arid regions. The major turfgrasses adapted to the cool humid regions, and irrigated areas of the cool arid regions, are species of *Agrostis, Poa, Festuca,* and *Lolium*. In the warm humid and irrigated areas of the warm arid regions, the major adapted turfgrasses are species of *Cynodon, Zoysia, Stenotaphrum, Eremochloa, Paspalum, Festuca,* and *Agropyron*. In the non-irrigated warm arid regions, species of *Buchloe* and *Bouteloua* are adapted.

Perennial ryegrass (*Lolium perenne* L.), also called English ryegrass, is a cool-season perennial bunchgrass native to Europe, temperate Asia, and North Africa. It is widely distributed throughout the world, including North and South America, Europe, New Zealand, and Australia. Perennial ryegrasses can be grown on their own for lawns in the northern regions, and are widely used as a mixture with permanent grasses or in new lawn establishment. They are also popular for winter overseeding quality Bermuda lawns, golf areas and sports fields while they are dormant in Southern states. Most golf course greens today are overseeded with perennial ryegrass for winter color cover and a better playing surface.

Perennial ryegrass lawns are one of the best lower maintenance lawns of the cool season grasses. Perennial ryegrass is one of the toughest and most wearable turf covers that can be grown. Perennial ryegrass is noted for quick germination, shiny green color, fine texture and dense forming sod. High disease and insect resistance help to make perennial ryegrass one of the leading choices for lawn and athletic covers in North America.

Perennial ryegrass is also mixed with other cool season grasses to provide more density and to rejuvenate the dominant grass in the mixture. Perennial ryegrass is often added to Kentucky bluegrass to add strength and give bluegrass time to repair while the perennial is in full growth. These two grass species can be mown at the same height and retain a sod density for which both are well known. (Dunn, J. H. et al. 1997. Tall fescue, Kentucky bluegrass, and perennial ryegrass blends and mixtures. In: Turfgrass Research and Information Report. Univ. Missouri-Columbia Turfgrass Research Center.)

Perennial ryegrass is important in forage/livestock systems. High palatability and digestibility make this species highly valued for dairy and sheep forage systems. As a result, it often is the preferred forage grass in temperate regions of the world. It is a valuable winter and spring grazing crop that can be overseeded onto additional forages or used alone lengthening the pasture season. Perennial ryegrass is a fast growing multi-use forage crop requiring minimal tillage and is competitive enough to make a place for itself. Its compact growing habit reinforces the ground and gives a perfect erosion base for pastures with heavy traffic and, in the case of heavy rains or snow meltdown, it helps keep livestock out of the mud as much as possible. Perennial ryegrass is fast germinating, grows prolifically, and can be grazed heavily. Many varieties have been developed and are in "prescription" mixes or in stand-alone crops for complete pasture and hay production. The ryegrasses are well known for being companion grasses in mixes of fescue, clovers, timothy, orchard grass and many other pasture crops. The ryegrass is usually first to germinate and grow in while the others are developing. Perennial ryegrass is used to overseed many warmer season pastures that may go dormant or are growing slower due to cooler temperatures. This is one of the most diversified grasses used in the forage industry for permanent and semi-permanent pastures. (Hannaway, D. et al. 1999. Perennial ryegrass (*Lolium perenne* L.). Pacific Northwest Extension Publication 502.)

Among northern turfgrasses, the main species grown for sod is Kentucky bluegrass (*Poa pratensis*). It is attractive and widely adapted to the central United States (e.g. Midwest), where it is almost exclusively used for all manner of turf areas. It is long lived, easy to mow, and relatively easy to maintain. It is preferred by sod producers, because it produces an abundance of underground, horizontal stems (rhizomes) that hold the sod together very well at maturity at about one to one-and-one-half years, and many varieties are readily available.

Kentucky bluegrass is, however, not without certain drawbacks: 1) it has a very slow germination of three weeks or longer in cool weather; 2) it is very slow to develop and seedlings are weak; 3) it is susceptible to common diseases such as smut, mildew, leaf spot, brown patch, and rusts of various types; 4) it lacks drought tolerance; 5) it is very slow to recover from disease or physical damage; 6) overseeding of old stands is very difficult and rarely successful.

Since the arrival of true turf-type perennial ryegrass varieties some 30 years ago with the varieties Manhattan and Pennfine, interest in perennial ryegrasses has significantly expanded world wide. They are not only used as seeded grasses, but even more so by sod producers and on large acreages. The newer varieties of today present several distinct advantages over Kentucky Bluegrass.

However, there are also some disadvantages to growing perennial ryegrasses. In particular, perennial ryegrass sod needs to be underlain with a very thin mono-filamentous net to hold the sod together for harvest since it does not produce sod-tying horizontal stems of any kind. The net must be cut out with every harvest and must be laid down again as the next crop is established. Remnants of the net tend to remain in the field after sod harvest and present a real problem for equipment readying the field for the next crop. These remnants tend to be picked up on axels and harrow tines, as well as wrap themselves tightly into bearings and cause the bearings to fail by over heating. In addition, perennial ryegrass is somewhat less heat and cold tolerant than Kentucky bluegrass.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided perennial ryegrass varieties which have spreading growth habits.

Another aspect of the invention is a perennial ryegrass having more than 1000 tillers per 100 $cm^2$.

According to the invention there is further provided a perennial ryegrass having between 1001 and 1050 live tillers per 100 $cm^2$.

Another aspect of the invention is a perennial ryegrass having between 1051 and 1100 live tillers per 100 $cm^2$.

According to the invention there is further provided a perennial ryegrass having between 1101 and 1150 live tillers per 100 $cm^2$.

Another aspect of the invention is a perennial ryegrass having a tiller length of greater than 3.5 cm.

According to the invention there is further provided a perennial ryegrass having a tiller length between 4.1 cm and 5.0 cm.

Another aspect of the invention is a perennial ryegrass having a tiller length between 5.1 cm and 6.0 cm.

According to the invention there is provided a perennial ryegrass of having a tiller length between 6.1 cm and 7.0 cm.

Another aspect of the invention is a perennial ryegrass having more than 11.0 nodes per tiller.

According to the invention there is further provided a perennial ryegrass having between 11.1 nodes and 12.0 nodes per tiller.

Another aspect of the invention is a perennial ryegrass having between 12.1 nodes and 13.0 nodes per tiller.

According to the invention there is further provided a perennial ryegrass having between 13.1 nodes and 14.0 nodes per tiller.

Another aspect of the invention is a perennial ryegrass having between 14.1 nodes and 15.0 nodes per tiller.

According to the invention there is provided a perennial ryegrass having between 15.1 nodes and 16.0 nodes per tiller.

Another aspect of the invention is a perennial ryegrass having one or more secondary tillers.

According to the invention there is further provided a perennial ryegrass having between 1.0 and 2.0 secondary tillers.

Another aspect of the invention is a perennial ryegrass having between 2.1 and 3.0 secondary tillers.

According to the invention there is further provided a perennial ryegrass having between 3.1 and 4.0 secondary tillers.

Another aspect of the invention is a perennial ryegrass with mature sod having a tensile strength between 75 lbs and 95 lbs.

According to the invention there is further provided a perennial ryegrass with mature sod having a tensile strength between 75 lbs and 80 lbs.

According to the invention there is further provided a perennial ryegrass with mature sod having a tensile strength between 80.1 lbs and 85 lbs.

According to the invention there is further provided a perennial ryegrass with mature sod having a tensile strength between 85.1 lbs and 90 lbs.

According to the invention there is further provided a perennial ryegrass with mature sod having a tensile strength between 90.1 lbs and 95 lbs.

DEFINITIONS

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Alter. Alter refers to the utilization of up-regulation, down-regulation, or gene silencing.

Backcrossing. Backcrossing is a process in which a breeder repeatedly crosses hybrid progeny back to one of the parents, for example, a first generation hybrid $F_1$ with one of the parental genotypes of the $F_1$ hybrid.

Cell. Cell as used herein includes a plant cell, whether isolated, in tissue culture or incorporated in a plant or plant part.

Commercial perennial ryegrass. A commercial perennial ryegrass is one which has been sold commercially.

Cotyledon. A cotyledon is a seed leaf.

Crown. The crown in grass is the area at which top growth and root growth originate.

Culm. The culm is the main aerial shoot to which leaves and inflorescences are attached. The culm is a rounded or slightly flattened stem with one or more solid joints known as nodes. The leaves are attached at the nodes and if the stem is not simple but branched, branches arise only at nodes. Roots may also develop from a node where the node comes into contact with the ground (as in decumbent and prostrate stems).

Embryo. The embryo is the small plant contained within a mature seed.

Endophyte. The term endophyte is applied to fungi which live within plant tissues for all or part of their lifecycle and cause no apparent infections.

Gene Silencing. The interruption or suppression of the expression of a gene at the level of transcription or translation.

Genotype. Refers to the genetic constitution of a cell or organism.

Grass flower or inflorescence. Flowers of grasses are borne in an inflorescence or flower head which terminates the culm and other branches of the stem. Smaller units of the inflorescence are called spikelets and these are arranged on one or more branches in a wide variety of different ways to which the standard terminology for inflorescences can be applied, but using the spikelet instead of the individual flower.

Hypocotyl. A hypocotyl is the portion of an embryo or seedling between the cotyledons and the root. Therefore, it can be considered a transition zone between shoot and root.

Internode. The internodes act as spacers that distance one node from another.

Intercalary meristem. Intercalary meristem is a meristem at the base of the internode in monocot stems (particularly grass stems).

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Mature sod. Means sod that is 8 to 14 months old after seeding, wherein sod is mature at 8 to 11 months old after a fall seeding and sod is mature at 12 to 14 months old after a spring seeding.

Node. A node in a grass stem is a solid point at which the intercalary meristem is located. The node also contains the bud that is capable of producing a new shoot. The terminal node contains the bud that produces the inflorescence.

Pedigree Distance. Pedigree distance refers to the relationship among generations based on their ancestral links as evidenced in pedigrees. Pedigree distance may be measured by the distance of the pedigree from a given starting point in the ancestry.

Percent Identity. Percent identity as used herein refers to the comparison of the homozygous alleles of two perennial ryegrass varieties. Percent identity is determined by comparing a statistically significant number of the homozygous alleles of two developed varieties. For example, a percent identity of 90% between perennial ryegrass variety 1 and perennial ryegrass variety 2 means that the two varieties have the same allele at 90% of their loci.

Percent Similarity. Percent similarity as used herein refers to the comparison of the homozygous alleles of one perennial ryegrass variety with another ryegrass plant, and if the homozygous allele of the first ryegrass matches at least one of the alleles from the other plant then they are scored as similar. Percent similarity is determined by comparing a statistically significant number of loci and recording the number of loci with similar alleles as a percentage. A percent similarity of 90% between the first ryegrass and another plant means that the first ryegrass matches at least one of the alleles of the other plant at 90% of the loci.

Plant. As used herein, the term "plant" includes reference to an immature or mature whole plant, including a plant from which seed, roots or leaves have been removed. Seed or embryo that will produce the plant is also considered to be the plant.

Plant Height. Plant height is taken from the top of the soil to the top node of the plant and is measured in centimeters.

Plant Parts. As used herein, the term "plant parts" (or a perennial ryegrass plant, or a part thereof) includes protoplasts, leaves, stems, roots, root tips, anthers, pistils, seed, embryo, pollen, ovules, cotyledon, hypocotyl, flower, shoot, tissue, petiole, cells, meristematic cells and the like.

Primary tillers. Primary tillers are shoots arising at the crown.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Rhizome. A rhizome is a modified stem that grows underground. Rhizomes are jointed (thus distinguishable from roots) with bladeless leaves (scales) arising from the joints. Rhizomes enable a grass plant to spread horizontally as new culms develop vertically from the joints. Thus, grasses with extensive rhizome development will form a turf rather than distinct tufts or bunches.

Secondary tillers. Secondary tillers are tillers arising as branches of the primary tillers.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Stolon. A stolon is a stem that creeps across the surface of the ground, and is really a basal branch of the culm that will develop roots and shoots from some or all of its nodes. Like a rhizome, a stolon results in a spreading or turf forming grass plant.

Tensile strength. Means the amount of force in pounds required to tear a piece of sod in two. Tensile strength is determined with a mechanical sod stretcher coupled to a device to measure force in pounds. Tensile strength, tear point and sod strength are used interchangeably.

Tiller. A tiller is another name for a grass stem.

Tiller length. Tiller length is measured in centimeters from the lowest node to the last node subtending the green foliage.

Vernalization. Vernalization induces plants to begin the reproductive cycle after exposure to cold temperatures and short day length. The amount of cold exposure and short day lengths required varies with the species.

DETAILED DESCRIPTION OF THE INVENTION

The newer commercial varieties of perennial ryegrass present several distinct advantages over Kentucky bluegrass: 1) perennial ryegrasses germinate within 6-7 days of sowing; 2) they establish very quickly from seed because of strong and rapid seedling development; 3) herbicides can be used to control one of the worst grassy weeds, annual bluegrass (*Poa annua*); 4) reduced disease susceptibility compared to Kentucky bluegrasses; 5) for the eastern United States, endophyte containing varieties are available to reduce damage from crown feeding insects. No endophyte is presently available in Kentucky bluegrass; 6) perennial ryegrass turf matures sufficiently within 7-8 months to permit sod harvest whereas Kentucky bluegrass needs 12-18 months; 7) perennial ryegrass tolerates more physical wear than Kentucky bluegrass; 8) perennial ryegrass recovers more quickly from disease and physical damage.

However, as noted above, the currently available perennial ryegrass varieties do not produce rhizomes or stolons and do not weave tightly together. Netting must be used to hold the sod together for harvest since it does not produce sod-tying horizontal stems of any kind. The net must be cut out with every harvest and must be laid down again as the next crop is established. Remnants of the net tend to remain in the field after sod harvest and present a real problem for equipment readying the field for the next crop. These remnants tend to be picked up on axels and harrow tines, as well as wrap themselves tightly into bearings and cause the bearings to fail by over heating.

In contrast, the perennial ryegrasses of the present invention produce "pseudo-stolons" a new and never before seen structure in commercial perennial ryegrass which allows the plants to tightly interweave thereby avoiding the requirement of netting. Use of the spreading perennial ryegrasses of the present invention allows sod fields to be established without a supporting net. The present invention will save the sod producers about $200 plus per acre in netting and labor, and they will also reduce equipment down time.

Grasses consist of crown, roots, leaves and stems. The crown is the dividing organ between roots and stems (positively geotropic vs. negatively geotropic). Grass stems and leaves form the canopy of turf. Grass stems (also called tillers) are composed of a series of nodes at which single leaves develop and internodes which develop from primordia laid down at the crown. Initially these tillers are sessile, meaning that nodes and internodes are closely stacked upon each other.

Grasses are monocotyledons that do not have an apical meristem such as the dicotyledons (beans, peas etc.). Instead they have what is called an internal meristem or intercalary growing point. This meristem is located above each node. Cell division occurs in an upside-down fashion when compared to conventional growth of apical meristems. The younger portion of the divided cell is deposited below the mother cell, rather than above it.

During normal vegetative growth (from seedling to vernalization during the cool and shorter daylight periods) the intercalary meristems generally remain dormant. There is minimal elongation to allow new leaves to begin to develop and elongate. Leaves also have their elongation point at their base where cells don't divide but elongate to account for leaf growth. Therefore, no significant stem elongation occurs during this vegetative cycle.

Vernalization is induced during the cool months of late fall and winter. It is the trigger for reproductive growth that manifests itself in telescoping out of the here-to-fore sessile tightly stacked nodes and internodes. At the top (terminal) node primordia develop that will become the inflorescence (seed spike). The spike will emerge after all the other intercalary and finite meristems have exhausted themselves; the stems stop elongating and reach maturity after setting seed and eventually the stems will die at or after seed harvest. Beyond harvest time, a perennial grass plant does not die entirely like an annual plant (wheat, etc.) instead it resumes some vegetative growth because the reproductive cycle is over. New primordia develop at the crown, and the two cycles repeat year after year.

Many turfgrasses require vernalization to reproduce by seed. After vernalization, the previously sessile grass nodes and internodes begin to telescope out, but in most uses of turf the development of the seed head from the terminal node is rarely seen because it is removed by mowing. This type of growth, (the seed bearing stem growing from the terminal node) is replaced by new vegetative growth from primordia at the crown on a regular basis, otherwise there would be nothing left of the plant but leafless stubble.

The present invention provides perennial ryegrass plants which differ from commercial perennial ryegrass plants in their growth when grown for seed production. As reproductive culms of the present invention elongate in spring after vernalization, they are at first upright but then turn horizontal, radiating flatly from the crown with a diameter of about 45 centimeters, and then again turn vertical at the $4^{th}$ or $5^{th}$ node to produce normal inflorescences. The ratio of reproductive culms of plants of the present invention to those of regular commercial perennial ryegrasses is about 2:1 indicating that a better than average seed yield potential is possible. After seed harvest, the lower portion of the culm of plants of the present invention (which generally escapes the mower during cutting to harvest the seed) remains alive and again begins to produce new shoots and roots at the decumbent nodes near the soil. If sufficient moisture is available, they in turn begin to elongate to form new tillers that continue vegetative growth during mild winters in a horizontal fashion, causing the plant to expand until the next reproductive cycle ensues. By contrast, the remaining stubble of regular commercial ryegrasses generally dies off completely and no further seed production will occur until the plants are vernalized again. In a few currently available varieties, the lower one or two nodes may produce small aerial plantlets, but differ from plants of the present invention in that the small aerial plantlets of the commercial ryegrasses do not make contact with the soil and eventually wither the following spring.

The present invention provides perennial ryegrass plants which differ in their growth from currently available perennial ryegrasses when grown for sod. Observations have shown that plants of the present invention form a tightly knit, dense, readily harvestable sod without netting within 7-8 months after fall seeding at a relatively low rate of 90-100 lbs/acre. Substantially higher seeding rates are used for regular perennial ryegrasses (200 lbs. plus), but the higher seeding rate is not needed with the ryegrasses of the present invention.

When grown for sod, the varieties of the present invention behave no differently than regular commercial perennial ryegrasses before the first vernalization period (winter after fall seeding). After vernalization, the initially tight stacks of nodes and internodes of the plants of the present invention begin to elongate, but, unlike currently available commercial ryegrasses, not in an upright fashion. Instead the plants of the present invention grow within and below the live green canopy surface and push out a new leaf and rootlets at each node, and even produce secondary branches which, in turn, continue growth as the initial stem; this is something that is not seen in currently available perennial ryegrasses. Each plant of the present invention is capable of producing many of the more or less horizontal stems developing quickly into a tightly intertwined mass above the soil that forms a very dense turf canopy. During this growth process, older nodes and their leaves are being shaded out by new growth hence the nodes lose their leaves and, to some extent, their roots, and wind up more or less naked below the surface canopy. Nevertheless, they remain alive and continue growth indefinitely. Only very rarely will a tiller in a plant of the present invention develop a terminal spike, and only then if the turf is not mown.

Once vernalization has taken place the ensuing vegetative growth in the plants of the present invention becomes indeterminate. Patches in older turf stands of the present invention, originating from a single seed, form very dense circular patterns that tend to exclude other grasses as well as resist weed invasion quite effectively. These patches continue to enlarge from year to year without ever producing a single seed head. As maturity is reached (after one winter), the initial crown of the individual plant is lost and replaced by the many filamentous pseudo-stolons that branch off from the initial anchor point. These filamentous stems often form branches and continue to elongate by adding more nodes (leaves, internodes, and axillary buds) during the growing season.

For the plants of the present invention, most of the buds remain dormant while the thin stems continue to elongate. The single leaves that are produced at the nodes quickly die off again due to shading by new growth. On occasion lateral buds will break dormancy and develop new vegetative branches again with leaves and filamentous roots that soon senesce. The result is a rather naked network of intertwining branches below a canopy of very dense leaves. At the surface several buds are active at the same time forming a very dense canopy that shades the area below so that no green leaves are left. Due to the continuous elongation of these filamentous stems during the growing season, the patches slowly enlarge from year to year.

This is different behavior from regular commercial perennial ryegrasses which retain their crowns over many years and become woody in the process. The behavior of plants of the present invention is also different from truly stoloniferous grasses such as creeping bentgrass and/or roughstalk bluegrass. The stolons of truly stoloniferous grasses remain flat on the soil surface and root down at almost every node where also new plantlets arise.

The perennial ryegrasses of the present invention, while spreading, are not considered invasive because their annual spread is slow compared to the rate of other creeping grass species such creeping bentgrass or roughstalk bluegrass. Nevertheless, they spread, and that is a completely new growth form in perennial ryegrass.

The type of spreading growth of the plants of the present invention defies conventional nomenclature in taxonomy. The tillers of the plants of the present invention do not appear to be true stolons (above ground creeping horizontal stems) since the elongating shoots of the present invention are usually not flat on the soil, but somewhat suspended between the canopy and the soil; hence the designation "pseudo-stoloniferous" may be appropriate.

EXAMPLES

The following examples are provided to further illustrate the present invention and are not intended to limit the invention beyond the limitations set forth in the appended claims.

Example 1

Characteristics of Perennial Ryegrass Plants of the Present Invention

The ryegrass plants of the present invention display a distinct difference from regular perennial ryegrass in that there is continued slow elongation of the horizontal vegetative tillers that are responsible for the increase of a single plant from year to year with 3.0 mm to 8.0 mm long internodes. Each node will produce a leaf with a dormant axillary bud. The leaf will shortly senesce when it is shaded out by further growth. Some axillary buds break dormancy and produce further vegetative branch tillers, so that a somewhat naked intertwining net is created. Nodes in regular perennial ryegrasses remain sessile during vegetative summer growing season and do not elongate until vernalized.

Table 1 shows some of the characteristics of perennial ryegrasses of the present invention. Characteristics were observed on multiple varieties of ryegrasses of the present invention in Aurora, Oreg.

TABLE 1

| | |
|---|---|
| Seed: | Relatively small to medium, within normal parameters, 250,000-265,000/lb |
| Germination: | Within six days under good conditions, similar to other perennial ryegrasses |
| Seedlings: | Quite aggressive and similar to other perennial ryegrasses |
| Texture (Leaf Width): | Initially like other perennial ryegrasses (0.2-0.3 cm), later becoming very fine (0.10-0.15 cm) |
| Color: | Medium to medium dark, depending on clonal and varietal differences |
| Culm Length: | 76-84 cm |
| Plant Diameter: | One year old - Average of 28 to 35 cm |
| Maturity (Seed Harvest): | Medium to medium late (mid July) depending on location and agronomic variables |
| Insects: | To date no insect damage has been noted |
| Diseases: | Moderately susceptible to stem rust; strong resistance to winter leaf spot, crown and stripe rust; no information on grey leaf spot to date |
| Drought tolerance: | Similar to other perennial ryegrasses |
| Shade Tolerance: | Similar to other perennial ryegrasses |
| Weed Control: | Will tolerate all chemicals that are recommended for regular perennial ryegrasses |
| Turf Growth Habit: | Initially similar to other perennial ryegrasses, then becoming very dense and fine with many horizontal tillers that intertwine tightly (pseudo-stolons) consisting of 10,000 plus live shoots/square foot after 8-10 months. As a contaminant in regular perennial ryegrass turf, tight uniform patches increase radially and tend to exclude other grasses and weeds. The turf is very attractive, particularly under close mowing (½"). |
| Growth Habit for Seed Production: | Seedlings initially upright; as reproductive tillers elongate (bolt) in spring after vernalization, stems become prostrate at first 4-5 nodes, then turn vertical and terminate in normal spikes; spikes contain 25-32 spikelets with 7-9 florets/spikelet. Seed production potential is normal to slightly higher because of high number of reproductive tillers which outnumber those of regular perennial ryegrass by 2:1 or more. |

Example 2

Number of Live Tillers

After vernalization, the perennial ryegrass plants of the present invention produce many tightly intertwined horizontal tillers within six to eight months (pseudo-stolons). This characteristic is more pronounced in spring after fall seeding and after winter vernalization than in summer after spring seeding. Nonetheless, these intertwining tillers grow vegetatively throughout the growing season and form a very dense sward of 10,000 tillers or more per square foot by season's end. This number is about 60% to 100% plus higher than for other good perennial ryegrasses. The turf produced by the plants of the present invention feels like a plush carpet under foot.

The very soft foliage does not shred in mowing, provided mower blades are sharp. Vertical elongation is somewhat less than in other turf type perennial ryegrasses, particularly during summer, but total clipping mass is about the same due to the greater turf density.

In Table 2, the tiller density of perennial ryegrass varieties of the present invention is compared with the tiller density of currently available commercial perennial ryegrass varieties. The comparison is of two- to three-year-old swards in July 2006 and 2007 in Aurora, Oreg. Column 1 shows the variety where SD-1 and SD-2 are varieties of the present invention and the remaining varieties are currently available commercial perennial grass varieties. Column 2 shows the number of live tillers per 100 cm in 2006 and column 3 shows the number of live tillers per 100 cm$^2$ in 2007.

TABLE 2

| | No. Live Tillers/100 cm$^2$ | |
|---|---|---|
| Variety | 2006 | 2007 |
| SD-1 | 1112 | 1127 |
| SD-2 | 1098 | 1076 |
| Covet | 491 | 486 |
| Devine | 543 | 571 |
| Pinstripe | 696 | 648 |
| Flash II | 536 | 503 |

As can be seen in Table 2, the perennial ryegrass varieties of the present invention produce significantly more tillers per 100 cm$^2$ than do the currently available commercial perennial ryegrass varieties. The number of live tillers per 100 cm$^2$ includes from 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149 to 1150 and all numbers inclusive.

Example 3

Tiller Characteristics

In table 3, a comparison of the tiller characteristics of perennial ryegrass plants of the present invention with commercially available perennial ryegrass plants is shown. Column 1 shows the variety with SD-2 Res., SD-5D, SD-10TC, LF-142 and LF-143 being varieties of the present invention and Casper, Buccaneer, Peak and Covet being currently available commercial perennial ryegrass plants. Column 2 shows the tiller length in centimeters as measured from the lowest node to the last node subtending the green foliage, column 3 shows the number of nodes per tiller, column 4 shows the number of primary tillers and column 5 shows the number of secondary tillers.

TABLE 3

Tiller Characteristics of Several Perennial Ryegrasses in Mature Turf in Western Oregon

| Variety/Selection | Tiller Length cm | No. of Nodes per Tiller | No. of Primary Tillers | No. of Secondary Tillers |
|---|---|---|---|---|
| SD-2 Res. | 5.17 | 15.3 | 2.2 | 1.2 |
| SD-5 D | 6.27 | 13.6 | 2.3 | 3.2 |
| SD-10 TC | 5.33 | 11.8 | 3.7 | 3.3 |
| LF-142 | 6.30 | 15.3 | 2.2 | 1.7 |
| LF-143 | 4.01 | 12.5 | 3.8 | 2.5 |
| Casper | 0.92 | 3.7 | 1.8 | 0 |
| Buccaneer | 0.45 | 3.0 | 5.0 | 0 |
| Peak | 0.62 | 3.2 | 4.0 | 0 |
| Covet | 1.33 | 5.7 | 1.2 | 0 |

As can be seen in table 3, the perennial ryegrasses of the present invention have tillers which are considerably longer than those of currently available commercial perennial ryegrasses. Tiller lengths include lengths of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, and 7.0 cm and all numbers inclusive.

In addition, the plants of the present invention have significantly more nodes per tiller and produce secondary tillers, a characteristic currently available commercial perennial ryegrasses do not have. The average number of nodes per tiller includes 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, and 16.0 and all numbers inclusive. The average number of secondary tillers includes 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0 and all numbers inclusive.

In addition to the perennial ryegrass varieties of the present invention listed in Tables 1 and 2, other varieties have also been developed. These additional varieties also display the spreading and tightly interweaving characteristics of the previously mentioned varieties.

Example 4

Sod Tensile Strength

The perennial ryegrass varieties of the present invention display considerably greater sod tensile strength when compared to currently available commercial perennial ryegrass varieties. Currently available commercial perennial ryegrass sod needs to be underlain with a very thin mono-filamentous net to hold the sod together for harvest since it does not produce sod-tying horizontal stems of any kind. Because of the unique growth habit of the ryegrass varieties of the present invention and because of its greater sod tensile strength, netting is not required in order to grow sod using any of the varieties of the present invention.

Table 4 shows a comparison of the tensile strength of the present invention in comparison to a blend of Kentucky Bluegrass varieties and eight varieties of regular perennial ryegrass. Column one shows the tensile strength of sod that is made up of four different varieties of Kentucky Bluegrass, with each variety making up 25% of the volume of the sod. Within column one, the left column shows the replication number and the right column shows the tear point in pounds (lbs). Column two shows the tensile strength of sod that is made up of the present invention, with SD-1 and SD-2 each accounting for 50% of the volume of the sod. Within column two, the left column shows the replication number and the right column shows the tear point in pounds (lbs). Column three shows the tensile strength of sod that is made up of eight single varieties of regular perennial ryegrass, with Casper, LF-142, Blackcat, Covet, Vador, Peak and Buccaneer each being tested separately. Within column three, the left column shows the varietal name and the right column shows the tear point in pounds (lbs). Regular perennial ryegrass means currently available commercial perennial ryegrass varieties.

TABLE 4

Sod Tensile Strength Test Comparison

| *Kentucky Bluegrass Blend 25% of each Variety of Impact, Chicago II Rugby II and New Destiny | | Spreading Per. Ryegrass Blend 50% of Variety SD-1 & SD-2 | | Regular Per. Ryegrass 8 single varieties 1 Replication each | |
|---|---|---|---|---|---|
| Replication | Tensile strength in lbs. | Replication | Tensile strength in lbs | Variety name | Tensile strength in lbs |
| 1 | 100 | 1 | 82 | Casper | 0 |
| 2 | 108 | 2 | 92 | LF-143 | 6 |
| 3 | 102 | 3 | 80 | Blackcat | 4 |
| 4 | 102 | 4 | 80 | LF-142 | 7 |
| 5 | 100 | 5 | 88 | Covet | 5 |
| 6 | 104 | 6 | 83 | Vador | 0 |
| 7 | 103 | 7 | 83 | Peak | 0 |
| 8 | 101 | 8 | 82 | Buccaneer | 0 |
| Average | 102.5 | | 83.8 | | 2.75 |

As can be seen in Table 4, the perennial ryegrasses of the present invention have a tensile strength that is similar to that of the Kentucky Bluegrass blend but is significantly stronger than regular perennial ryegrasses with an average tear point of 102.5 (lbs) for the Kentucky Bluegrass blend, 83.8 (lbs) for the perennial ryegrasses of the present invention and 2.75 lbs for regular perennial ryegrasses. Tensile strength is in pounds and includes 70.4, 71.6, 72.8, 73.4, 75.4, 78.9, 81.2, 87.4, 88.5, 89.4, 90.1, 91.2, 92.4, 94.1, 95.8, 96.4 and 98.2 and all numbers inclusive.

FURTHER EMBODIMENTS OF THE INVENTION

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation are referred to herein collectively as "transgenes". In some embodiments of the invention, transgenic variants of the spreading ryegrass varieties of the present invention may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed spreading ryegrass varieties of the present invention.

One embodiment of the invention is a process for producing spreading ryegrass varieties further comprising a desired trait, said process comprising transforming a spreading ryegrass plant with a transgene that confers a desired trait. Another embodiment is the product produced by this process. In one embodiment the desired trait may be one or more of herbicide resistance, insect resistance, or disease resistance. The specific gene may be any known in the art or listed herein, including: a polynucleotide conferring resistance to imidazolinone, sulfonylurea, glyphosate, glufosinate, triazine, benzonitrile, cyclohexanedione, phenoxy proprionic acid and L-phosphinothricin; a polynucleotide encoding a *Bacillus thuringiensis* polypeptide, or a polynucleotide conferring resistance to one or more nematodes, *Phytophthora* root rot, or other fungi, or one or more viruses.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (*Maydica* 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A genetic trait which has been engineered into the genome of a particular spreading ryegrass plant may then be moved into the genome of another ryegrass variety using traditional breeding techniques that are well known in the plant breeding arts. For example, a backcrossing approach is commonly used to move a transgene from a transformed ryegrass variety into an already developed ryegrass variety, and the resulting backcross conversion plant would then comprise the transgene(s).

Various genetic elements can be introduced into the plant genome using transformation. These elements include, but are not limited to genes, coding sequences, inducible, constitutive, and tissue specific promoters, enhancing sequences, and signal and targeting sequences. For example, see the traits, genes and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed spreading ryegrass plants using transformation methods as described below to incorporate transgenes into the genetic material of the spreading ryegrass plant(s).

Expression Vectors for Spreading Ryegrass Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., *Plant Physiol.* 86:1216 (1988), Jones et al., *Mol. Gen. Genet.*, 210:86 (1987), Svab et al., *Plant Mol. Biol.* 14:197 (1990), Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., *Somatic Cell Mol. Genet.* 13:67 (1987), Shah et al., *Science* 233:478 (1986), Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci. USA* 84:131 (1987), DeBlock et al., *EMBO J.* 3:1681 (1984)).

In vivo methods for visualizing GUS activity that do not require destruction of plant tissue are available (Molecular Probes publication 2908, IMAGENE GREEN, p. 1-4 (1993) and Naleway et al., *J. Cell Biol.* 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science* 263: 802 (1994)). GFP and mutants of GFP may be used as screenable markers.

Expression Vectors for Spreading Ryegrass Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters—An inducible promoter is operably linked to a gene for expression in soybean. Optionally, the inducible promoter is operably linked to a nucleotide sequence encoding a signal sequence which is operably linked to a gene for expression in perennial ryegrass. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *Proc. Natl. Acad. Sci. USA* 90:4567-4571 (1993)); In2 gene from maize which responds to benzenesulfonamide herbicide safeners (Hershey et al., *Mol. Gen. Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. USA* 88:0421 (1991)).

B. Constitutive Promoters—A constitutive promoter is operably linked to a gene for expression in perennial ryegrass or the constitutive promoter is operably linked to a nucleotide sequence encoding a signal sequence which is operably linked to a gene for expression in ryegrass.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2: 163-171 (1990)); ubiquitin (Christensen et al., *Plant Mol. Biol.* 12:619-632 (1989) and Christensen et al., *Plant Mol. Biol.* 18:675-689 (1992)); PEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters—A tissue-specific promoter is operably linked to a gene for expression in ryegrass. Optionally, the tissue-specific promoter is operably linked to a nucleotide sequence encoding a signal sequence which is operably linked to a gene for expression in ryegrass. Plants transformed with a gene of interest operably linked to a tissue-specific promoter produce the protein product of the transgene exclusively, or preferentially, in a specific tissue. Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., *Science* 23:476-482 (1983) and Sengupta-Gopalan et al., *Proc. Natl. Acad. Sci. USA* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of a protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.* 20:49 (1992); Knox, C., et al., *Plant Mol. Biol.* 9:3-17 (1987); Lerner et al., *Plant Physiol.* 91:124-129 (1989); Frontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

Wang et al. discuss "Large Scale Identification, Mapping and Genotyping of Single-Nucleotide Polymorphisms in the Human Genome", *Science*, 280:1077-1082, 1998, and similar capabilities are becoming available for the ryegrass genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of interest. Through the transformation of ryegrass the expression of genes can be altered to enhance disease resistance, insect resistance, herbicide resistance and other traits. DNA sequences native to ryegrass as well as non-native DNA sequences can be transformed into ryegrass and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) *PNAS USA* 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Likewise, by means of the present invention, additional genes of interest can be expressed in transformed plants. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al. *Cell* 78:1089 (1994) (*Arabidopsis* RSP2 gene for resistance to *Pseudomonas syringae*), McDowell & Woffenden, (2003) *Trends Biotechnol.* 21(4): 178-83 and Toyoda et al., (2002) *Transgenic Res.* 11 (6):567-82.

B. A gene conferring resistance to a pest, such as a nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*); Chattopadhyay et al. (2004) *Critical Reviews in Microbiology* 30 (1): 33-54 2004; Zjawiony (2004) *J Nat Prod* 67 (2): 300-310; Carlini & Grossi-de-Sa (2002) *Toxicon*, 40 (11): 1515-1539; Ussuf et al. (2001) *Curr Sci.* 80 (7): 847-853; and Vasconcelos & Oliveira (2004) *Toxicon* 44 (4): 385-403. See also U.S. Pat. No. 5,266,317 to Tomalski et al., which discloses genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene, U.S. Pat. Nos. 7,145,060, 7,087,810 and 6,563,020.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 and U.S. Pat. No. 5,580,852, which disclose peptide derivatives of tachyplesin which inhibit fungal plant pathogens, and PCT application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology,* 5(2) (1995); Pieterse & Van Loon (2004) *Curr. Opin. Plant Bio.* 7(4):456-64 and Somssich (2003) *Cell* 113(7):815-6.

U. Antifungal genes. See Cornelissen and Melchers, *Plant Physiol.,* 101:709-712 (1993); Parijs et al., *Planta* 183:258-264 (1991) and Bushnell et al., *Can. J. of Plant Path.* 20(2):137-149 (1998). Also see U.S. Pat. No. 6,875,907.

V. Detoxification genes, such as for fumonisin, beauvericin, moniliformin and zearalenone and their structurally related derivatives. For example, see U.S. Pat. No. 5,792,931.

W. Cystatin and cysteine proteinase inhibitors. See U.S. Pat. No. 7,205,453.

X. Defensin genes. See WO 03/000863 and U.S. Pat. No. 6,911,577.

Y. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexanediones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. No. 10/427,692. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

5. Genes that Create a Site for Site Specific DNA Integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of *E. coli* (Enomoto et al., 1983), and the R/RS system of the pSR1 plasmid (Araki et al., 1992).

6. Genes that Affect Abiotic Stress Resistance.

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. No. 10/817,483 and U.S. Pat. No. 6,992,237 where cytokinin expression is modified resulting in plants with increased stress tolerance, such as drought tolerance, and/or increased yield. Also see WO 02/02776, WO 2003/052063, JP2002281975, U.S. Pat. No. 6,084,153, WO 01/64898, U.S. Pat. Nos. 6,177,275 and 6,107,547 (enhancement of nitrogen utilization and altered nitrogen responsiveness). For ethylene alteration, see US 20040128719, US 20030166197 and WO 2000/32761. For plant transcription factors or transcriptional regulators of abiotic stress, see e.g. US 20040098764 or US 20040078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29123, U.S. Pat. No. 6,794,560, U.S. Pat. No. 6,307,126 (GAI), WO 99/09174 (D8 and Rht), and WO 2004/076638 and WO 2004/031349 (transcription factors).

Methods for Ryegrass Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994)).

Following transformation of ryegrass target tissues, expression of the above-described selectable marker genes allows for preferential selection of transformed cells, tissues and/or plants, using regeneration and selection methods well known in the art.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" *Crop Science* 39:1464-1490 (1999), and Berry et al., Assessing Probability of Ancestry Using Simple Sequence Repeat Profiles: Applications to Maize Inbred Lines and Soybean Varieties" *Genetics* 165:331-342 (2003).

Particular markers used for these purposes are not limited to any particular set of markers, but are envisioned to include any type of marker and marker profile which provides a means of distinguishing varieties.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present.

Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Tissue Culture

Further reproduction of the spreading ryegrass varieties of the present invention can occur by tissue culture and regeneration. Tissue culture of various tissues of spreading ryegrass and regeneration of plants therefrom is well known and widely published. For example, reference may be had to Bradley, D. E. et al. 2001. Effects of cultivar, explant treatment, and medium supplements on callus induction and plantlet regeneration in perennial ryegrass. *Int. Turfgrass Soc. Res. J.* 9:152-156; Cao, M. X., et al. 2006. Transformation of recalcitrant turfgrass cultivars through improvement of tissue culture and selection regime. *Plant, Cell, Tissue Organ Culture.* 85:307-316; WenZhen, L. et al. Factors effecting on tissue culture of perennial ryegrass (*Lolium perenne* L.). *Forest Res.* 2004. 17:95-101. Thus, another aspect of this invention is to provide cells which upon growth and differentiation produce spreading ryegrass plants having the physiological and morphological characteristics of the spreading ryegrass plants of the present invention.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, culms, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

DEPOSIT INFORMATION

A deposit of the spreading ryegrass disclosed above and recited in the appended claims has been made with the American Type Culture Collection (ATOC), 10801 University Boulevard, Manassas, Va. 20110. This deposit is made up of spreading ryegrass lines, including SD-1 and SD-2, containing the trait for spreading ryegrass as disclosed herein. The date of deposit was Nov. 15, 2007. The deposit of 2,500 seeds was taken from the same deposit maintained by Ledeboer Farms since prior to the filing date of this application. All restrictions upon the deposit have been removed, and the deposit is intended to meet all of the requirements of 37 C.F.R. 1.801-1.809. The ATCC accession number is PTA-8792. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A perennial ryegrass having between 1000 and 1150 live tillers per 100 $cm^2$, representative seed has been deposited under ATCC Accession No. PTA-8792.

2. The perennial ryegrass of claim 1 having between 1001 and 1050 live tillers per 100 $cm^2$.

3. The perennial ryegrass of claim 1 having between 1051 and 1100 live tillers per 100 $cm^2$.

4. The perennial ryegrass of claim 1 having between 1101 and 1150 live tillers per 100 $cm^2$.

5. The perennial ryegrass of claim 1 having a tiller length of greater than 3.5 cm.

6. The perennial ryegrass of claim 5 having a tiller length between 4.1 cm and 5.0 cm.

7. The perennial ryegrass of claim 5 having a tiller length between 5.1 cm and 6.0 cm.

8. The perennial ryegrass of claim 5 having a tiller length between 6.1 cm and 7.0 cm.

9. The perennial ryegrass of claim 1 having more than 11.0 nodes per tiller.

10. The perennial ryegrass of claim 9 having between 11.1 nodes and 12.0 nodes per tiller.

11. The perennial ryegrass of claim 9 having between 12.1 nodes and 13.0 nodes per tiller.

12. The perennial ryegrass of claim 9 having between 13.1 nodes and 14.0 nodes per tiller.

13. The perennial ryegrass of claim 9 having between 14.1 nodes and 15.0 nodes per tiller.

14. The perennial ryegrass of claim 9 having between 15.1 nodes and 16.0 nodes per tiller.

15. The perennial ryegrass of claim 1 having one or more secondary branches per tiller.

16. The perennial ryegrass of claim 15 having between 1.0 and 2.0 secondary tillers.

17. The perennial ryegrass of claim 15 having between 2.1 and 3.0 secondary tillers.

18. The perennial ryegrass of claim 15 having between 3.1 and 4.0 secondary tillers.

19. The perennial ryegrass of claim 1 with mature sod having a tensile strength between 75 lbs and 95 lbs.

20. The perennial ryegrass with mature sod of claim 19 having a tensile strength between 75 lbs and 80 lbs.

21. The perennial ryegrass with mature sod of claim 19 having a tensile strength between 80.1 lbs and 85 lbs.

22. The perennial ryegrass with mature sod of claim 19 having a tensile strength between 85.1 lbs and 90 lbs.

23. The perennial ryegrass with mature sod of claim 19 having a tensile strength between 90.1 lbs and 95 lbs.

24. The perennial ryegrass of claim 1, wherein said perennial ryegrass has a spreading growth habit.

* * * * *